United States Patent [19]

Kremer et al.

[11] 4,000,271
[45] Dec. 28, 1976

[54] DEODORIZED ORGANOTHIOPHOSPHORUS COMPOUNDS WITH REDUCED TOXICITY

[75] Inventors: Ross A. Kremer, Belle Mead; David A. Pearce, Edison, both of N.J.

[73] Assignee: Mobil Oil Corporation, New York, N.Y.

[22] Filed: Aug. 25, 1972

[21] Appl. No.: 283,866

[52] U.S. Cl. .............................. 424/225; 424/212; 424/213; 424/223; 424/365
[51] Int. Cl.$^2$ ............................................ A01N 9/36
[58] Field of Search .................... 424/76, 225, 318; 260/989

[56] References Cited

UNITED STATES PATENTS

| | | | |
|---|---|---|---|
| 2,970,080 | 1/1961 | Oros et al. ........................ | 424/24 X |
| 3,268,393 | 8/1966 | Wilson ........................... | 424/365 X |
| 3,309,432 | 3/1967 | English .............................. | 260/989 |

FOREIGN PATENTS OR APPLICATIONS 676,776   8/1952   United Kingdom

*Primary Examiner*—Leonard Schenkman
*Attorney, Agent, or Firm*—Charles A. Huggett; Howard M. Flournoy

[57] ABSTRACT

Certain organothiophosphorus compounds in combination with (1) effective amounts of a deodorizing agent selected from linoleic acid, linolenic acid and drying oils such as linseed or tung oil containing same, and/or mixtures thereof and (2) effective amounts of a stabilizing agent selected from alkylene or polyalkylene glycols not only result in deodorizing such normally malodorous organothiophosphorus compounds and stabilizing them against decomposition but unexpectedly provide reduced toxicity.

3 Claims, No Drawings

DEODORIZED ORGANOTHIOPHOSPHORUS COMPOUNDS WITH REDUCED TOXICITY

CROSS-REFERENCE TO RELATED APPLICATIONS

Copending application Ser. No. 63,293, filed Aug. 12, 1970 now U.S. Pat. No. 3,961,043 and entitled Deodorization of Organothiophosphorus Compounds.

BACKGROUND OF THE INVENTION

1. Field of the Invention

This invention is directed to novel compositions comprising normally malodorous organothiophosphorus compounds (e.g., organothiophosphates and organothiophosphites such as S,S-dipropyl O-ethyl phosphorodithioate and S,S-diethyl O-ethyl phosphorodithioite) and linoleic acid, linolenic acid, drying oils (e.g., linseed oil and tung oil) and drying oils containing linoleic acid and linolenic acid or mixtures of linoleic acid and linolenic acid to deodorize such organothiophosphorus compounds, and an alkylene or polyalkylene glycol such as propylene glycol to stabilize the organothiophosphorus compounds against decomposition when in contact with solid or granular carriers therefor.

2. Description of the Prior Art

U.S. Pat. No. 3,112,244 discloses a method for controlling nematodes with certain phosphorodithioites and phosphorodithioates, and U.S. Pat. No. 3,268,393 discloses a method for killing insects with certain phosphorodithioites and phosphorodithioates. It is well known in the art that certain aldehydes (i.e., U.S. Pat. No. 3,309,432), peroxides (i.e., U.S. Pat. No. 2,879,284), metallic salts or complexes (i.e., British Pat. No. 960,013) and compounds containing unsaturated tertiary carbons (i.e., Netherlands application No. 6,412,188) may be used for deodorization of certain organothiophosphorus compounds.

Solid carriers, e.g., powdered or granular clay, of the type commonly used in formulating pesticides, such as organothiophosphates, exert a chemical breakdown on the organic phosphate. This has the effect of degrading or decomposing the phosphate when mixed therewith. Although this is a slow process the effect of the carrier on the phosphate over prolonged periods of time, as during storage, tend to reduce its pesticidal effect below satisfactory field condition levels. It is well known in the art that certain alkylene or polyalkylene glycols may be used (i.e., U.S. Pat. No. 2,970,080) to stabilize particular types of phosphorodithioates on clay carriers. However, an adverse effect of these hydroxy compounds when used as stabilizers in granular or solid compositions of organothiophosphorus compounds according to the invention, is their tendency to increase the dermal mammalian toxicity of such compositions.

Applicants surprisingly have discovered a means of deodorizing these compositions and of stabilizing granular formulations of them while concomitantly decreasing mammalian dermal toxicity.

SUMMARY OF THE INVENTION

This invention provides for pesticidally effective compositions comprising mixtures of (1) a normally malodorous organothiophosphorus compound of the formula:

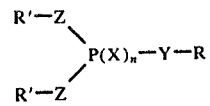

wherein R is a member selected from the group consisting of hydrogen, alkyl (e.g., $C_1$–$C_8$), substituted alkyl (e.g., $C_1$–$C_8$), phenyl, alkyl-substituted phenyl, halo-substituted phenyl, phenyl-substituted phenyl and carbethoxyalkyl, R' is a member selected from the group consisting of alkyl (e.g., $C_1$–$C_8$), X is a member selected from the group consisting of =O and =S, $n$ is the integer 0 or 1, and Y and Z are not in the same and are members selected from the group consisting of oxygen and sulfur, (2) an amount, sufficient to deodorize said organothiophosphorus compound, of a material selected from the group consisting of linoleic acid, linolenic acid, a drying oil such as linseed oil and/or a mixture of linoleic acid and linolenic acid and/or said drying oil and (3) an amount sufficient to stabilize said organothiophosphorus compounds against decomposition selected from alkylene or polyalkylene glycols; pesticidal compositions comprising said aforementioned mixtures having reduced dermal toxicity; and said pesticidal compositions with a solid carrier therefor. This invention more specifically provides for compositions comprising a normally malodorous organothiophosphorus compound and the synergistic combination of a deodorizing agent such as linseed oil and a stabilizing agent such as an alkylene or polyalkylene glycol and a solid carrier therefor.

DESCRIPTION OF SPECIFIC EMBODIMENTS

As will be noted, the compounds for use in the compositions of the present invention are organothiophosphorus compounds which normally have a characteristic objectionable odor and the advantageous combination of a deodorizing compound and a stabilizing compound. Non-limiting examples of organothiophosphorus compounds which may be used in the mixture according to the present invention include compounds having the general structure:

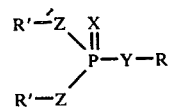

wherein R, R', X, Y and Z are as hereinbefore defined, such as:

S,S-dibutyl O-methyl phosphorodithioate,
S,S-dipropyl O-ethyl phosphorodithioate,
S,S-dipropyl O-methyl phosphorodithioate,
S,S-diethyl O-ethyl phosphorodithioate,
S,S-dipropyl O-propyl phosphorodithioate,
S,S-dibutyl O-ethyl phosphorodithioate,
S,S-dimethyl O-ethyl phosphorodithioate,
S,S,-dibutyl O-butyl phosphorodithioate,
S,S-dipropyl O-butyl phosphorodithioate, S-(1,2-dicarbethoxyethyl) O,O-dimethyldithiophosphite, S-(1,3-dicarbethoxypropyl) O,O-dimethyldithiophosphate, and
S-(1,2-dicarbethoxyethyl) O,O-diethyldithiophosphate, and compounds having the general structure:

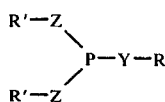

wherein R, R', Y and Z are as hereinbefore defined, such as:

S,S-diethyl O-ethyl phosphorodithioite,
S,S-diethyl O-o-tolyl phosphorodithioite,
S,S-diethyl O-m-tolyl phosphorodithioite,
S,S-dipropyl O-propyl phosphorodithioite,
S,S-dibutyl O-ethyl phosphorodithioite,
S,S-diethyl O-methyl phosphorodithioite,
S,S-dipropyl O-methyl phosphorodithioite,
S,S-dipropyl O-ethyl phosphorodithioite,
S,S-dipropyl O-2-chloroethyl phosphorodithioite,
S,S-dipropyl O-m-tolyl phosphorodithioite,
S,S-dipropyl O-2,4-dichlorophenyl phosphorodithioite,
S,S-dipropyl O-p-chlorophenyl phosphorodithioite,
S,S-dibutyl O-propyl phosphorodithioite,
S,S-dibutyl O-butyl phosphorodithioite, and
S,propyl S-butyl O-tolyl phosphorodithioite.

Non-limiting examples of deodorizing compounds or agents which may be used in the compositions of the present invention include, linoleic acid and linolenic acid, and mixtures thereof, drying oils, and/or drying oils containing one or more of said acids, as for example linseed oil and tung oil. These deodorizing compounds according to the invention must be capable of oxidative polymerization upon exposure to air.

Non-limiting examples of stabilizing compounds or agents useful in this invention include alkylene and polyalkylene glycols such as ethylene glycol, propylene glycol, butylene glycol, diethylene glycol, triethylene glycol, polyethylene glycol and the like.

The compositions according to the invention containing the disclosed deodorizing and stabilizing agents are thus deodorized, stabilized and unexpectedly reduced in mammalian dermal toxicity.

In the formulation of the compositions of the present invention, and particularly when the composition is to be used as a pesticide, the deodorizing compound and the stabilizing compound and the organothiophosphorus compound are preferably mixed as liquids. The concentration of the components in the formulation is fixed such that they are miscible when blended but upon subsequent exposure to air the deodorizing agent, e.g., drying agent and/or component thereof, polymerizes and is no longer miscible with the liquid mixture. When the composition is desired for use as a pesticide, the resulting liquid mix may then be combined with solid carriers by spraying the mixture thereon to provide a pesticide in granular form.

Reduction of the dermal toxicity is apparently achieved in the compositions containing the combination of the stabilizing agent and an air polymerizable deodorizing agent comprising a drying oil, one or more of the above-mentioned acids and/or a combination of both in the following manner. For example, the drying oil or a component thereof polymerizes upon exposure to an oxygen atmosphere, separates out and coats the organothiophosphorus-glycol layer. This coating apparently controls the rate of release of the phosphorus compound from the carrier sufficiently to substantially reduce dermal toxicity.

The composition of the present invention may be used in various ways to achieve pesticidal action according to the particular organothiophosphorus compound used. They may be applied as dusts, as liquid sprays, or as gas-propelled sprays, and may contain, in addition to a solid carrier, additives such as emulsifying agents, wetting agents, binding agents, gases compressed to the liquid state, stabilizers and the like. A wide variety of solid carries may be used in the pesticidal compositions. Non-limiting examples of solid carriers include talc, bentonite, diatomaceous earth, pyrophyllite, fuller's earth, gypsum, flours derived from cottonseeds and nut shells, and clays selected from the class of kaolin clays, montmorillonite clays, attapulgite clays and the like.

In practice, pesticidal compositions containing pesticidally effective amounts of the inventive compositions may be prepared in the form of concentrates, which are diluted in the field to the concentration desired for application. For example, the concentrate mixture can be a wettable powder containing large amounts of organothiophosphorus compound, a solid carrier (e.g., attapulgite or other clay), and wetting and dispersing agents. Such powders can be diluted prior to application by dispersing them in water to obtain a sprayable suspension containing the concentration of organothiophosphorus compound desired for application. Thus, it is within the contemplation of this invention to provide pesticidal compositions containing up to about 80 percent, by weight of the composition, of organothiophosphorus compound. Accordingly, depending upon whether it is ready for application or it is in concentrated mixture form, the contemplated pesticidal composition contains between about 1 percent and 80 percent, by weight of the composition of at least one organothiophosphorus compound derivative and a solid carrier as defined hereinbefore.

Although the amount of the deodorizing agent that may be used may be varied over a rather wide range as long as the desired deodorization is effected, satisfactory results are generally obtained by use of the deodorizing agent in an amount up to about 50% by weight of the organothiophosphorus compound and, more specifically, in an amount of from about 5 to about 30% by weight of the organothiophosphorus compound.

The amount of the stabilizing agent may also vary over a wide range as long as the desired stabilization is effected, satisfactory results are generally obtained by use of the stabilizing material in an amount up to about 100% or more specifically about 10 to 60% by weight of the organothiophosphorus compound.

The following examples demonstrate typical procedures of formulation of deodorized and stabilized dry organothiophosphorus compounds.

EXAMPLE I

One part of boiled linseed oil was mixed with five parts of liquid S,S-dipropyl O-ethyl phosphorodithioate at room temperature. After mixing, a granular product was formulated containing about 10% of the organothiophosphorus compound by spraying the liquid mixture onto granular Attaclay (attapulgite clay) of 24/48 mesh in an enclosed rotating drum.

EXAMPLE II

Two and one-half parts of propylene glycol was mixed with 5 parts of liquid S,S-dipropyl O-ethyl phosphorodithioate at room temperature. After mixing a granular product was formulated as in Example I.

EXAMPLE III

One part boiled linseed oil and 2½ parts of propylene glycol were mixed with 5 parts of S,S-dipropyl O-ethyl phosphorodithioate at room temperature. After mixing a granular product was formulated as in Example I.

EXAMPLE IV

This example illustrates the reduced dermal mammalian toxicity of compositions according to the invention. Pesticide compositions were prepared according to Examples I, II and III. They were then tested for acute dermal toxicity on white rabbits at a level of 400 mg. of the granular compositions per kg. of rabbit weight.

The testing method used was in accordance with a standardized test procedure reported in *Appraisal of the Safety of Chemicals in Foods, Drugs and Cosmetics* by the staff of the Division of Pharmacology Food, Drug Administration, Department of Health, Education and Welfare, published 1959 by The Association of Food and Drug Officials of the United States, Austin 1, Tex., in an article entitled Dermal Toxicity by J. H. Draize. Beginning on page 54 of said publication, Dr. Draize discloses the acute dermal toxicity test procedure used in detail.

The compositions of the examples were subjected to the standard pesticidal tests for which each respective organothiophosphorus compound is known to have activity. The results of such testing showed that the mixing of the organothiophosphorus compound with the deodorizing compound and the stabilizing compound used in the present invention did not adversely affect pesticidal activity and, in some instances, prolonged or increased such activity.

Therefore, as shown in Table hereinabove, the composition of Example III containing the combination of both the stabilizing agent and the deodorizing agent according to the invention had the improved stability and low odor expected but quite expectedly had significantly lower dermal toxicity than expected. The dermal toxicity was lower than the Examples containing the organothiophosphorus compound without either the glycol or the linseed oil. In this regard it is to be noted that the composition without the glycol stabilizer resulted in the death of two out of four rabbits exposed to it; the composition without the linseed oil deodorizer resulted in the death of four out of four rabbits exposed to it. On the otherhand the composition with both the linseed oil deodorizer and the glycol stabilizer caused the death of only one out of four rabbits exposed to it.

Although the present invention has been described with preferred embodiments, it is to be understood that modifications and variations may be resorted to, without departing from the spirit and scope of this invention, as those skilled in the art will readily understand.

What is claimed is:

1. A nematocidally and insecticidally effective composition comprising between about 1 and about 80% by weight of the composition of S,S-dipropyl O-ethyl phosphorodithioate; from about 5 to about 30%, by weight of the phosphorodithioate, of boiled linseed oil sufficient to deodorize said phosphorodithioate; and from about 10 to about 60%, by weight of the phosphorodithioate, of propylene glycol sufficient to stabilize said phosphorodithioate whereby the composition had reduced dermal toxicity relative to such a composition devoid of said boiled linseed oil or propylene glycol.

2. The composition of claim 1 comprising a solid clay carrier therefor.

3. The composition of claim 2 where the carrier is attapulgite clay.

TABLE

DERMAL TOXICITY OF GRANULAR FORMULATIONS OF ORGANOTHIOPHORUS COMPOUNDS ON WHITE RABBITS

| Example | ORGANOTHIOPHOSPHORUS COMPOUND* | PROPYLENE GLYCOL | BOILED LINSEED OIL | DEATHS OF WHITE RABBITS AT DERMAL DOSAGE OF 400 mg/kg |
|---|---|---|---|---|
| I | yes | no | yes | 2/4 |
| II | yes | yes | no | 4/4 |
| III | yes | yes | yes | 1/4 |

*88% Purity, S,S-Dipropyl O-ethyl phosphorodithioate